United States Patent [19]  
Zelaskowski et al.

[11] 3,955,927  
[45] May 11, 1976

[54] TRACE LEAD ANALYSIS METHOD

[75] Inventors: Catherine A. Zelaskowski, Trenton, N.J.; John J. Carlisi, Langhorne, Pa.

[73] Assignee: Mobil Oil Corporation, New York, N.Y.

[22] Filed: Feb. 12, 1975

[21] Appl. No.: 549,221

Related U.S. Application Data

[63] Continuation-in-part of Ser. No. 371,338, June 18, 1973, abandoned.

[52] U.S. Cl. .......................... 23/230 R; 23/230 HC; 23/230 M
[51] Int. Cl.$^2$ ................... G01N 31/22; G01N 33/22
[58] Field of Search ........ 23/230 R, 230 HC, 230 M

[56] References Cited
OTHER PUBLICATIONS

Snyder et al., "A New Field Method for the Determination of Organolead Compounds in Air," Anal. Chem. Vol. 33, No. 9, Aug. 1961, pp. 1175–1180.

Henderson et al., "Rapid Spectrophotometric Determination of Triethyllead, Diethyllead, and Inorganic Lead Ions, and Application to the Determination of Tetraorganolead Compounds," Anal. Chem. Vol. 33, No. 9 Aug. 1961, pp. 1172–1175.

Pilloni et al., "Spectrophotometric Determination of Diethyllead and Diethyltin Ions with 4-(2-Pyridylazo)Resorcinol," Anal. Chim. Acta, 35 (1966) pp. 325–329.

Pilloni, "Complexes of Organolead and Organotin Ions With 1-(2-pyridylazo)-2-Naphthol," Anal. Chim. Acta, 37 (1967) pp. 497–507.

Pollard et al., "4-(2-Pyridylazo)-Resorcinol as a Possible Analytical Reagent for the Colorimetric Estimation of Cobalt, Lead and Uranium," Anal. Chim. Acta, 20 (1959), pp. 26–31.

*Primary Examiner*—Morris O. Wolk
*Assistant Examiner*—Barry I. Hollander
*Attorney, Agent, or Firm*—C. A. Huggett; R. W. Barclay; S. A. Strober

[57] ABSTRACT

The trace lead content of gasoline, specifically in lead concentrations of about 0.01 to 0.10 grams of lead per U.S. gallon of gasoline, is determined colorimetrically by the steps of mixing an iodine solution with the gasoline, subjecting the mixture to ultra-violet light and adding an indicator solution containing 4-(2-pyridylazo)-resorcinol disodium salt with agitation and comparing the resulting color to standard indicator solutions.

8 Claims, No Drawings

TRACE LEAD ANALYSIS METHOD

CROSS-REFERENCE TO RELATED APPLICATIONS

This application is a continuation-in-part application of U.S. Ser. No. 371,338 filed on June 18, 1973, and now abandoned.

BACKGROUND OF THE INVENTION

1. Field of the Invention

This invention relates to a method of determining the lead content found in trace amounts in unleaded gasoline. In particular, the method relates to a rapid field analysis of the lead content in gasoline by colorimetric comparison.

2. Description of the Prior Art

The availability of unleaded gasoline to modern motorists is a subject of increased industrial effort among gasoline suppliers. The marketing operations for unleaded gasoline, however, involve shipment over present distributive facilities which also carry leaded gasoline. Accordingly, lead is still present in pipelines, tank cars, tank trucks, in service station pumps and reservoirs and the like. Coupled with this is a prospective governmental fine which may be exacted for failure of the gasoline supplier to keep the lead content in unleaded gasoline below a certain maximum, such as 0.05 grams per gallon. Accordingly, it would be advantageous to make rapid on-the-spot analyses of gasoline samples for lead which may have been picked up during shipment of the gasoline and to permit non-technical personnel to carry out these analyses.

It is known, in Pilloni et al, *Anal. Chim. Acta*, 35 (1966) pages 325–329, to produce complex colored products by reacting diethyllead ion with the monosodium salt of 4-(2-pyridylazo)-resorcinol. This reaction is carried out in a buffered solution and a pH of about 9. The ions were produced from diethyllead dichloride. Also, similar disclosure is made by Dagnall et al in *Talanta*, Vol. 12 (1965) pages 583–588. Reference is also made to the text of Shapiro and Frey, *The Organic Compounds of Lead*, John Wiley & Sons, New York (1968), in particular, pages 75, 77, 266 and 302, which mentions organolead salts and the reaction with chelates.

None of the aforesaid references discloses a single, rapid yet exact method of determining a range of concentrations of lead in trace amounts in gasoline.

SUMMARY OF THE INVENTION

We have now discovered a rapid method for analyzing the trace concentration of lead in unleaded gasolines by the steps of treating a gasoline containing trace amounts of an organolead compound with a halogen compound, subjecting the mixture to ultraviolet radiation for a short period of time and then adding an aqueous solution of a pyridylazo hydroxyaryl compound to produce in the resulting aqueous phase a chromogenic response involving a range of colors from yellow to red, each of said colors relating to a particular lead concentration.

DESCRIPTION OF SPECIFIC EMBODIMENTS

In the analytical method of this invention, lead salts normally found in gasoline are converted to an organolead halide salt. The usual commercial lead alkyls are tetramethyllead, tetraethyllead, dimethyldiethyllead, trimethylethyllead, and triethylmethyllead in varying concentrations. These lead compounds will react with a halogen to produce first a monohalide, then the dihalide and finally, after an extended period of time, the inorganic lead halide salt. While the tetraorganolead is soluble in gasoline, the dihalide is water soluble and, hence, any colorimetric analysis may occur in the water phase rather than in the gasoline phase. Quite often, gasolines are dyed red, green and the like for identification purposes, and colorimetric analysis in such medium would be misleading, or at best inexact. On the other hand, the aqueous phase, which would normally be colorless, would provide an excellent colorimetric analysis medium for comparison with standard color solutions. Conversion to the inorganic halide has been found to be too slow and cumbersome involving heating, phase separations and so forth. As hereinafter discussed, conversion to the dihalide can generally be performed quickly and requires no special techniques on the part of the operator.

Of the halogens, iodine in a form of a solution in a polar organic solvent is the most preferred reagent. Such solvents as chloroform, ether, acetone, methylethylketone, and the lower alkyl alcohols, of preferably 1 to 3 carbon atoms, may be used as a solvent in this invention. Of particular interest in this invention are solutions using chloroform or methanol. The use of chlorine or bromine is less satisfactory, mainly because of the handling problems encountered with compounds of these halogens. Applying chlorine gas or hydrochloric acid would require considerable equipment and safety precautions. It is understood that in this initial step, most or all of the tetraorganolead is converted to the monohalide and dihalide.

The resulting mixture is then exposed to ultra-violet radiation, ranging from 2800 to below 4000 angstroms (or "A"), such as from a 3660A wavelength ultra-violet source, for a period ranging from at least about one minute to ten minutes, and preferably from about one minute to about five minutes. At least one edge of the sample vial should be within one inch of the ultra-violet source. The power of conventional bulbs used herein is about 4 watts. For example, a 3-minute exposure is satisfactory for a glass vial of one ounce, and one-inch diameter and 1/16-inch wall thickness. In this container, for the said length of time, most organolead compounds will react further with the iodine to produce the dialkyllead diiodide. It is understood that other vials might require correspondingly different exposure times to obtain the desired result. However, the exposure should be equivalent to a one to five minute exposure to a 3660A, 4-watt ultra-violet bulb, the closest distance of the sample vial being from zero to one inch away and the furthest being from 1 inch to 2 inches away from the bulb.

The test sample is then removed from the ultra-violet light. To the sample is added an aqueous solution of a pyridylazo hydroxyaryl compound or its metal salt. The hydroxy-portion of the molecule may be phenol, resorcinol, naphthol and the like. The metal salts, particularly sodium, potassium, and lithium are most preferred. Certain alkaline earth metal salts may be used, such as calcium, strontium or barium, although these salts are less preferred because they may have lower solubility in water. In any case, any of the alkali or alkaline earth metal salts of these pyridylazo hydroxyaryl compounds may be used. The disodium salt of pyridylazo resorcinol (or PAR-Na), is most preferred.

While it is possible to obtain a colorimetric reaction using the non-salt indicators, such as pyridylazo resorcinol (or PAR), they are less preferred because of their lower water solubility.

After addition of PAR-Na in an aqueous solution to the test sample, the mixture is agitated. Using small test samples contemplated in this invention, a vial or bottle of the sample may be shaken by hand. This agitation would assure that all of the diorganolead dihalide enters the water phase and would promote the formation of the PAR-Na-lead alkyl complex, the PAR-Na acting as a chelating ligand.

The pH of the reaction mixture which includes the test sample and the indicator solution is preferably in the range of about 6 to 10, most preferably from 9 to 10. Accordingly, it may be desirable to include buffers or pH control agents in the indicator solution along with the PAR-Na. For this purpose, there may be added salts or other compounds which would not react with the indicator. Such salts as sulfites, nitrates and hypochlorites of alkali metal and ammonium are suitable in this invention. One formulation contemplated in this invention is a solution containing PAR-Na, sodium sulfite, ammonium nitrate and ammonia in water. This solution is satisfactory for analysis of gasolines containing most lead alkyls or mixtures there of PAR-Na alone in water is sufficient when the lead alkyl is known.

It is understood that in photochemical reactions, such as the formation of the dihalide in the method of this invention, the wavelength and the intensity of the ultra-violet source may be important factors. However, we believe that control of light intensity is not a limiting factor in this invention. Since the concentration of organolead salts in the gasoline is very low the sample being tested is small and the test vial has relatively short distances, the wavelength range, the time of exposure and the distance of the test vial from the source adequately describes this step of the method of this invention.

The concentrations of iodine in solution are in the range of from about 0.2 to about 10 grams per liter of polar organic solvent solution. The concentration of the pyridylazo hydroxyaryl or metal salt in water is in the range from about 5 mg to about 50 mg per liter, and preferably from about 5 to about 10 mg per liter, of water solution.

The concentrations of the lead compound in gasoline which would be detected in this invention range from about 0.01 grams to about 0.10 grams or higher of lead per gallon of gasoline. These concentrations correspond to the color and intensity of the aqueous phase due to the formation of the complexed lead alkyl.

In a typical procedure, 5 ml of gasoline containing MLA 500 (5.7% tetramethyllead, 23.8% trimethylethyllead, 37.5% dimethyldiethyllead, 26.2% triethylmethyllead and 6.8% tetraethyllead) are added to a 1-ounce glass vial. Then 1 ml of iodine solution consisting of 0.5 grams of iodine per liter of chloroform is added. The vial is placed in a compartment, preferably at least partially enclosed, and an ultraviolet light source of 3660A wavelength ("GE F4T5.BL") in a 4-watt fixture, connected to a standard A.C. outlet is directed onto it for 3 minutes, the vial resting horizontally on the bulb.

Following the UV exposure, the vial is removed and 10 ml of a solution of 4-(2-pyridylazo)-resorcinol disodium salt in water, (at a concentration of 10 mg per liter), is added. The vial is shaken by hand for about 30 seconds. The color in the lower aqueous phase corresponds to the concentration of lead in the original gasoline sample as listed in Table 1.

TABLE 1

| Lead Content, g/Gal. | PAR-Na — Water Phase Color |
|---|---|
| 0.00 – 0.02 | Yellow |
| 0.03 – 0.04 | Yellow-orange |
| 0.05 – 0.06 | Orange |
| 0.07 – 0.10 | Orange-red |
| Greater than 0.10 | Red |

In order to determine the lead content in an unknown gasoline sample, the color of the lower aqueous phase is compared to previously standardized color comparison means.

The color comparison means may be a set of papers or cards or plastic surfaces having the gamut of colors from yellow to red. One preferred comparison means is a colorimeter in which the amount of complexed lead, such as PAR-Na lead alkyl, is measured. Alternatively, water solutions containing inorganic pigments may also be preferred because of cost.

Any inorganic salt which forms a color in water may be used to produce the standard color stock solutions useful in this invention. For the purpose of this invention, at least two solutions, one yellow and one red, are required. We have found that a water solution of cobalt chloride with a minor amount of hydrochloric acid provides a satisfactory red solution. This stock solution may be prepared by dissolving 25 grams of cobalt chloride hexahydrate in 500 ml of a 1% hydrochloric solution in the water. A satisfactory yellow solution is prepared by dissolving 1.2259 grams of dried potassium dichromate in 1 liter of water. In the case of the aforementioned example (with MLA 500) these two solutions of cobalt chloride and potassium dichromate are mixed in various proportions as set forth in Table 2 and diluted to 25 ml with water to prepare color standards:

TABLE 2

| Lead Content, g/Gal. | Cobalt Chloride, ml | Potassium Dichromate, ml |
|---|---|---|
| 0.02 | 4.0 | 4.0 |
| 0.03 | 6.0 | 4.0 |
| 0.05 | 10.0 | 3.0 |
| 0.07 | 14.0 | 3.0 |
| 0.10 | 17.0 | 1.0 |

For other lead alkyls or mixtures thereof other color standards may similarly be prepared or other color intensities be instrumentally measured.

The equipment necessary to carry out the method of this invention is uniquely applicable to a small, convenient test kit to be used by any field personnel. Premixed reagents can be supplied. Sample bottles and dropper pipettes or other measuring devices appropriately marked for adding the gasoline, the iodine solution, and the chelating solution, in correct volume are equally feasible. Moreover, a guarded ultra-violet lamp with a timing device may be fitted into a field kit. Standard color solutions or a colorimeter can be included as well.

The present invention has been described in detail with regard to specific embodiments, however, it is apparent that the method of this invention should not be restricted to such embodiments but should include any obvious modifications and variations thereof. Therefore, the present invention should not be limited in any way except as recited in the appended claims:

We claim:

1. A method for colorimetrically determining the lead content in gasoline by converting the tetraalkyllead in a gasoline to a dialkyllead diiodide comprising reacting the tetraalkyllead with iodine and exposing the resulting reaction mixture to ultraviolet radiation of 2800A to below 4000A whereby said dialkyllead diiodide is formed, adding a pyridylazo hydroxyaryl compound in aqueous solution to the gasoline to produce a color in the aqueous phase corresponding to the initial lead concentration.

2. The method of claim 1 wherein the pyridylazo hydroxyaryl compound is a pyridylazo resorcinol metal salt selected from the group consisting of alkali and alkaline earth metal salt.

3. The method of claim 2 wherein the salt is pyridylazo resorcinol disodium salt.

4. The method of claim 1 wherein the pyridylazo hydroxyaryl compound is an alkali metal salt of pyridylazo naphthol.

5. The method of claim 1 wherein the pH of the indicator solution is between 6 and 10.

6. The method of claim 1 wherein the iodine is in a solution of a polar solvent selected from the group consisting of chloroform, acetone and alcohols having from 1 to 3 carbon atoms.

7. The method of claim 1 wherein the ultraviolet exposure is from a 3660A wavelength 4-watt bulb ultraviolet source for a period of from 1 minute to 5 minutes.

8. The method of claim 1 wherein the gasoline sample being exposed to the ultraviolet radiation is contained in a vial at least one edge of which is within one inch from the ultraviolet source.

* * * * *

UNITED STATES PATENT AND TRADEMARK OFFICE
CERTIFICATE OF CORRECTION

PATENT NO. : 3,955,927
DATED : May 11, 1976
INVENTOR(S) : CATHERINE A. ZELASKOWSKI AND JOHN J. CARLISI

It is certified that error appears in the above–identified patent and that said Letters Patent are hereby corrected as shown below:

Column 3, line 45            "10" should be --30--

Signed and Sealed this

Eighth Day of February 1977

[SEAL]

Attest:

RUTH C. MASON
*Attesting Officer*

C. MARSHALL DANN
*Commissioner of Patents and Trademarks*